United States Patent
Goto et al.

(10) Patent No.: US 10,525,230 B2
(45) Date of Patent: Jan. 7, 2020

(54) SLEEP ASSISTANCE APPARATUS, SLEEP ASSISTANCE SYSTEM, AND SLEEP ASSISTANCE METHOD

(71) Applicant: SONY CORPORATION, Tokyo (JP)

(72) Inventors: Yoshio Goto, Kanagawa (JP); Tomoko Katsuhara, Kanagawa (JP); Yukari Tsunoda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 102 days.

(21) Appl. No.: 15/505,125

(22) PCT Filed: Jul. 9, 2015

(86) PCT No.: PCT/JP2015/003472
§ 371 (c)(1),
(2) Date: Feb. 20, 2017

(87) PCT Pub. No.: WO2016/031119
PCT Pub. Date: Mar. 3, 2016

(65) Prior Publication Data
US 2018/0177975 A1     Jun. 28, 2018

(30) Foreign Application Priority Data
Aug. 26, 2014   (JP) .................... 2014-171828

(51) Int. Cl.
*A61M 21/02*     (2006.01)
*A61B 5/16*      (2006.01)
(Continued)

(52) U.S. Cl.
CPC ............... *A61M 21/02* (2013.01); *A61B 5/16* (2013.01); *A61B 5/4809* (2013.01);
(Continued)

(58) Field of Classification Search
CPC .......... A61M 21/02; A61M 2021/0027; A61M 2021/0022; A61M 2021/0044;
(Continued)

(56) References Cited

U.S. PATENT DOCUMENTS

2013/0303837 A1* 11/2013 Berka .................. A61M 21/02
600/28

FOREIGN PATENT DOCUMENTS

| JP | 07-67964 A | 3/1995 |
|----|------------|--------|
| JP | 07-067964 A | 3/1995 |

(Continued)

OTHER PUBLICATIONS

International Search Report and Written Opinion of PCT Application No. PCT/JP2015/003472, dated Aug. 25, 2015, 10 pages of English Translation and 9 pages of ISRWO.
(Continued)

*Primary Examiner* — Christine H Matthews
(74) *Attorney, Agent, or Firm* — Chip Law Group (57) ABSTRACT

This sleep assistance apparatus includes a stimulation generation unit that generates stimulation, a user being capable of receiving the stimulation; a detection unit that detects biological information of the user; and a control unit that decides optimal stimulation on the basis of the detected biological information, and causes the stimulation generation unit to generate the optimal stimulation.

8 Claims, 7 Drawing Sheets

(51) Int. Cl.
*A61B 5/00* (2006.01)
*A61M 21/00* (2006.01)

(52) U.S. Cl.
CPC ... *A61B 5/4818* (2013.01); *A61M 2021/0022* (2013.01); *A61M 2021/0027* (2013.01); *A61M 2021/0044* (2013.01); *A61M 2021/0083* (2013.01); *A61M 2205/0216* (2013.01); *A61M 2205/0266* (2013.01); *A61M 2205/50* (2013.01); *A61M 2205/505* (2013.01); *A61M 2205/52* (2013.01); *A61M 2209/088* (2013.01); *A61M 2230/06* (2013.01); *A61M 2230/08* (2013.01); *A61M 2230/10* (2013.01); *A61M 2230/18* (2013.01); *A61M 2230/42* (2013.01); *A61M 2230/50* (2013.01); *A61M 2230/63* (2013.01)

(58) Field of Classification Search
CPC ........ A61M 2230/005; A61M 2230/10; A61M 2021/0066; A61M 21/00; A61M 2230/40; A61B 5/4812; A61B 5/4818; A61B 5/0476
See application file for complete search history.

(56) References Cited

FOREIGN PATENT DOCUMENTS

| JP | 2000-079149 A | 3/2000 |
|----|---------------|--------|
| JP | 2003-210587 A | 7/2003 |
| JP | 2010-035860 A | 2/2010 |
| JP | 2012-065996 A | 4/2012 |

OTHER PUBLICATIONS

International Preliminary Report on Patentability of PCT Application No. PCT/JP2015/003472, dated Mar. 9, 2016, 8 pages of English Translation and 5 pages of IPRP.

\* cited by examiner

SLEEP ASSISTANCE APPARATUS, SLEEP ASSISTANCE SYSTEM, AND SLEEP ASSISTANCE METHOD

CROSS REFERENCE TO RELATED APPLICATIONS

This application is a U.S. National Phase of International Patent Application No. PCT/JP2015/003472 filed on Jul. 9, 2015, which claims priority benefit of Japanese Patent Application No. JP 2014-171828 filed in the Japan Patent Office on Aug. 26, 2014. Each of the above-referenced applications is hereby incorporated herein by reference in its entirety.

TECHNICAL FIELD

The present technology relates to a sleep assistance apparatus, a sleep assistance system, and a sleep assistance method that provide satisfactory sleep to a user on the basis of biological information of the user.

BACKGROUND ART

As an apparatus that induces sleep, those that apply stimulation caused by sound to a user, receive a reaction to the applied stimulation from the user who performs a conscious operation, and organize stimulation to be applied to the user by analyzing the reaction have been known (see Patent Literature 1).

According to this Patent Literature 1, for example, synthetic sound whose volume is gradually reduced is given to the user at a constant period as stimulation at the initial stage of sleep. The user presses a button of a joystick as a conscious reaction of listening to the synthetic sound. When the user is in a sleep state, the reaction from the user is lost. The apparatus analyzes this condition, and records the time and elapsed time to sleep, for example. Further, the apparatus analyzes general-purpose data from the user to generate stimulation that produce more favorable effects.

CITATION LIST

Patent Literature

Patent Literature 1: Japanese Patent Application Laid-open No. 2003-210587

DISCLOSURE OF INVENTION

Technical Problem

The sleep process mainly includes stages of sleep introduction, sleep, and awakening from sleep. Therefore, the favorable sleep process is achieved by rapid sleep introduction, deep sleep, and favorable awakening from sleep. However, these problems are not sufficiently solved even if they are individually considered. For example, the method of using stimulation caused by sound can break the sleep of others depending on the sleep environment of the user. Further, because it depends on the user's conscious reaction, it has a bad usability.

In view of the circumstances as described above, it is an object of the present technology to provide a sleep assistance apparatus, a sleep assistance system, and a sleep assistance method that are superior in user's convenience and performance.

Solution to Problem

In order to solve the above-mentioned problem, a sleep assistance apparatus according to an embodiment of the present technology includes:

a stimulation generation unit that generates stimulation, a user being capable of receiving the stimulation;

a detection unit that detects biological information of the user; and a control unit that decides optimal stimulation on the basis of the detected biological information, and causes the stimulation generation unit to generate the optimal stimulation.

The control unit may be configured to cause the stimulation generation unit to generate a plurality of kinds of stimulation in order, evaluate the detected biological information every time the stimulation is generated, and determine the optimal stimulation for sleep introduction.

The control unit may be configured to determine presence or absence of generation of a failure factor for sleep on the basis of the detected biological information during the sleep, and cause the stimulation generation unit to generate specific stimulation when the generation of the failure factor is detected.

The detection unit may be configured to detect sound derived from the user during the sleep as the biological information, and the control unit may be configured to determine presence or absence of the generation of the failure factor for sleep on the basis of the detected sound.

The detection unit may be configured to detect a breathing rate of the user during the sleep as the biological information, and the control unit may be configured to determine presence or absence of the generation of the failure factor for sleep on the basis of the detected breathing rate.

The stimulation generation unit, the stimulation generation unit, and the control unit may be integrally formed as a unit that is freely attached and detached to/from the user.

Advantageous Effects of Invention

As described above, according to the present technology, it is possible to provide a sleep assistance apparatus that is superior in user's convenience, performance, and the like.

It should be noted that the effect described here is not necessarily limitative and may be any effect described in the present disclosure.

MODE(S) FOR CARRYING OUT THE INVENTION

Hereinafter, embodiments of the present technology will be described with reference to the drawings.

<First Embodiment>

[1. Conceptual Configuration of Sleep Assistance Apparatus]

Figure 1:
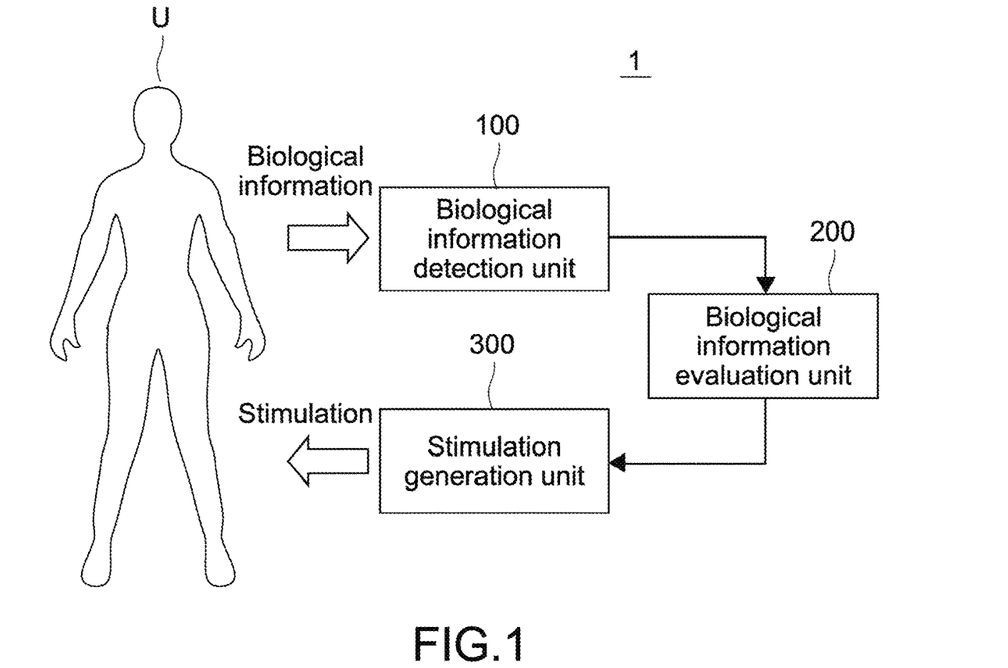
FIG. 1 A block diagram showing a functional configuration of a sleep assistance apparatus 1 according to a first embodiment to which the present technology is applied.

FIG. 1 is a block diagram showing a functional configuration of a sleep assistance apparatus 1 (sleep assistance system) according to a first embodiment to which the present technology is applied.

As shown in the figure, the sleep assistance apparatus 1 (sleep assistance system) includes a biological information detection unit 100, a biological information evaluation unit 200, a stimulation generation unit 300, and the like.

The biological information detection unit 100 detects the biological information from the human body of a user U.

The biological information evaluation unit 200 evaluates the biological information detected by the biological information detection unit 100, and determines tactile stimulation or environmental stimulation, which is favorable in each stage of the sleep process of the user U.

The stimulation generation unit 300 gives the favorable stimulation determined by the biological information evaluation unit 200 to the user U.

Next, the biological information detection unit 100, the biological information evaluation unit 200, and the stimulation generation unit 300 will be described in more detail.

[2. Biological Information Detection Unit 100]

The biological information detection unit 100 is configured by using one or more sensors that are in contact with or attached to the user U or are placed in an environment in which there is the user U. In more detail, the biological information detection unit 100 detects at least one of the following biological information.

(Body Motion)

Body motion represents the movement of the body of a user during sleep. The body motion is large when one falls asleep (at the time of sleep introduction), and is smaller as the sleep gets deeper. The body motion can be detected by using a motion sensor such as an acceleration sensor.

(Heart Rate)

A heart rate generally gets lower as the state of the sleep gets deeper. A sensor measures the heart rate by detecting a change occurred on the surface of the human body along with heartbeat as a change in light, pressure, sound, or the like.

(Breathing Rate)

A breathing rate gets lower as the state of the sleep gets deeper. A sensor measures, as a change in pressure, the breathing rate by detecting the state of breathing such as movement of contraction of breast. The method of measuring the breathing rate is particularly effective in the case where an apnea symptom is detected.

(Brain Waves)

Brain waves are detected by, for example, attaching an electrode of an electroencephalograph to a head. During awakening, an alpha wave and various waveforms having frequencies higher than those during sleep are mixed in the brain waves. In the sleep state, the alpha wave is reduced and a theta wave having a frequency lower than that of the alpha wave appears. In a deeper sleep state, a delta wave is generated.

(Body Temperature)

A body temperature gets generally lower as the sleep gets deeper.

(Electromyogram)

An electromyogram measures a change in potential caused by the muscle activity of a human body. The muscle activity is active during awakening. During sleep, the muscle activity is reduced, and thus, the potential is reduced. Further, although a part of the muscle activity lasts during REM sleep, the value of the electromyogram is at the substantially lowest level during non-REM sleep (deep sleep).

(Sound)

Sound is effective for detecting snoring, bruxism, or the like of the user during sleep.

In addition thereto, eyeball movement and the like may be detected. The eyeball movement can be detected by, for example, analyzing an image of the eyeballs of the user U, which is picked up by an imaging apparatus. It can be detected that the user gets sleepy, by using the pattern or speed of the eyeball movement, frequency or speed of blinking, and the like.

Note that by analyzing the image of the user U, it is also possible to acquire parameters such as body motion and a breathing rate similarly.

[3. Biological Information Evaluation Unit 200]

The biological information evaluation unit 200 is formed of, for example, a computer including a CPU (Central Processing Unit), a memory, and the like. In the memory, a program executed by the CPU and various kinds of data are stored. The CPU acquires biological information from the biological information detection unit 100 by executing the program stored in the memory, evaluates the biological information, and decides stimulation to be generated by the stimulation generation unit 300.

Now, the sleep process will be considered in terms of stages of falling asleep (sleep introduction), sleep, and wake-up (awakening from sleep).

In general, when one falls asleep (at the time of sleep introduction), the level of detection parameters such as body motion, a heart rate, a breathing rate, a body temperature, and an electromyogram is gradually reduced. The biological information evaluation unit 200 supplies a control command to the stimulation generation unit 300 so that stimulation that is suitable for the sleep introduction is given to the user U. Note that the stimulation that is suitable for the sleep introduction is stimulation that is suitable for relaxing the user U. In general, slow-tempo stimulation has a relaxing effect, and speedy, strong stimulation has an awakening effect.

Such stimulation that is suitable for relaxing the user U has an individual difference, and is different on different days even for one user U in some cases. In the biological information evaluation unit 200, waveform patterns of a plurality of kinds of stimulation for sleep introduction are prepared in advance. The biological information evaluation unit 200 causes the stimulation generation unit 300 to generate the plurality of kinds of stimulation in order, evaluates the biological information acquired from the biological information detection unit 100 every time the stimulation is generated, and decides the optimal stimulation.

During sleep, the level of detection parameters such as body motion, a heart rate, a breathing rate, a body temperature, and an electromyogram is kept lower than that during awakening.

Further, as a symptom that blocks the sound sleep of the user U, snoring, bruxism, an apnea symptom, and the like have been known. The biological information detection unit 100 includes a microphone for detecting snoring, bruxism, and the like from sound, and a respirometer for detecting an apnea symptom.

When detecting sound of snoring, bruxism, or the like from the data of sound acquired from the biological information detection unit 100, the biological information evaluation unit 200 causes the stimulation generation unit 300 to generate stimulation having strength higher than that of the stimulation for the sleep introduction. Further, the biological information evaluation unit 200 causes the stimulation generation unit 300 to generate stimulation having high strength similarly in the case where the breathing rate per unit time acquired from the biological information detection unit 100 is lower than the value determined in advance. The user U unconsciously reacts with the stimulation given at this time, and changes the posture or position of the body by himself/herself. Thus, snoring, bruxism, an apnea symptom, and the like can be temporarily prevented from occurring.

The wake-up (awakening from sleep) is comfortable when it occurs during REM sleep. In this regard, the biological information evaluation unit 200 estimates the cycle of REM sleep by detection parameters such as a heart rate, a breathing rate, a body temperature, an electromyogram, and brain waves, and estimates the REM sleep time closest to set get-up time before the set get-up time on the basis of the estimation result of the REM cycle and get-up time set by the user U in advance. The biological information evaluation unit 200 performs control so that the stimulation generation unit 300 is caused to generate stimulation that is suitable for get-up at the estimated REM sleep time.

[4. Stimulation Generation Unit 300]

The stimulation generation unit 300 gives various kinds of stimulation to the user U on the basis of the control command from the biological information evaluation unit 200.

Examples of stimulation given to the user U include visual stimulation, auditory stimulation, and thermal sense stimulation, in addition to tactile stimulation that is received by the user U through a tactile sense. The stimulation is received by the user U as stimulation to which a reaction is psychologically or biologically different depending on the strength or the way the strength is changed, i.e., the difference in parameters such as amplitude, a frequency, acceleration, an interval, and rhythm.

Further, the stimulation generation unit 300 may be one that uses home appliance equipment. The home appliance equipment only has to be an apparatus that is capable of giving some kind of stimulation to the sensory receptor of the user U, such as a television, a personal computer, a radio receiver, illumination equipment, an air conditioner, an alarm clock, an alarm, and an opening/closing apparatus of a curtain. The home 丆 ӿ È A P a p è ⓌΨ ς Γ Π ℰ 丆 ӿ È A P a p è Ⓦ Ψς Γ Π ℰ 丆 ӿ includes an interface unit that receives a control command from the biological information evaluation unit 200 through wireless or wired communication, a controller that controls the function of the home appliance equipment so that stimulation is given to the user U on the basis of the control command received by the interface unit, and a program that causes the controller to function as the stimulation generation unit 300.

[5. Specific Configuration Example of Sleep Assistance Apparatus 1]

Figure 2:
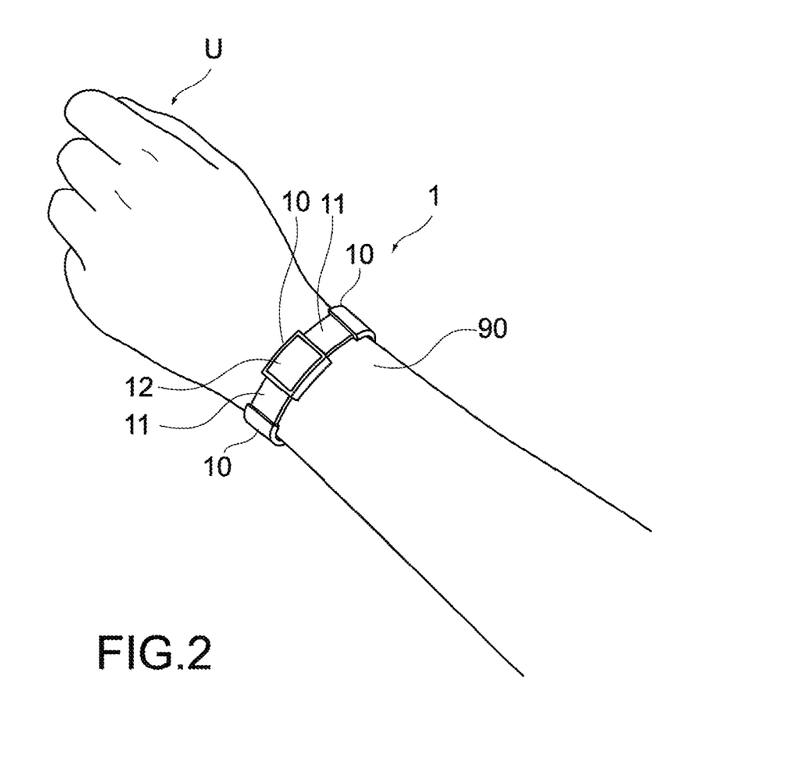
FIG. 2 A perspective view showing a configuration example of the sleep assistance apparatus 1 according to this embodiment.

FIG. 2 is a perspective view showing a specific configuration example of the sleep assistance apparatus 1.

The sleep assistance apparatus 1 in this specific example is a bracelet-type apparatus that can be attached to a wrist 90 of a human (user U), for example. As the stimulation generation unit 300, one that generates tactile stimulation is employed.

The present technology is not limited to a bracelet-type one, and may be those configured to be able to be attached to various parts from which the user U can obtain a tactile sense, such as a finger, neck, ankle, body, and head. Further, it may be provided in a form where a tactile sense can be obtained in a wider range of a human body, such as a clothing-type one and a bedding-type one.

This sleep assistance apparatus 1 includes a plurality of actuator mounting units 10 on which respective actuators are mounted and a plurality of belts 11 (coupling belts) that couple the actuator mounting units 10 to each other in series so that one bracelet is formed as a whole. The plurality of actuator mounting units 10 are coupled to each other at, for example, regular intervals in series via the belts 11.

To the actuator mounting units 10 or the belts 11, one or more sensors (whose illustration is omitted in FIG. 2) for detecting the biological information are provided.

To at least one of the plurality of actuator mounting units 10, a controller (whose illustration is omitted in FIG. 2), a display 12 with a touch panel as the user interface unit, and the like are provided.

Figure 3:
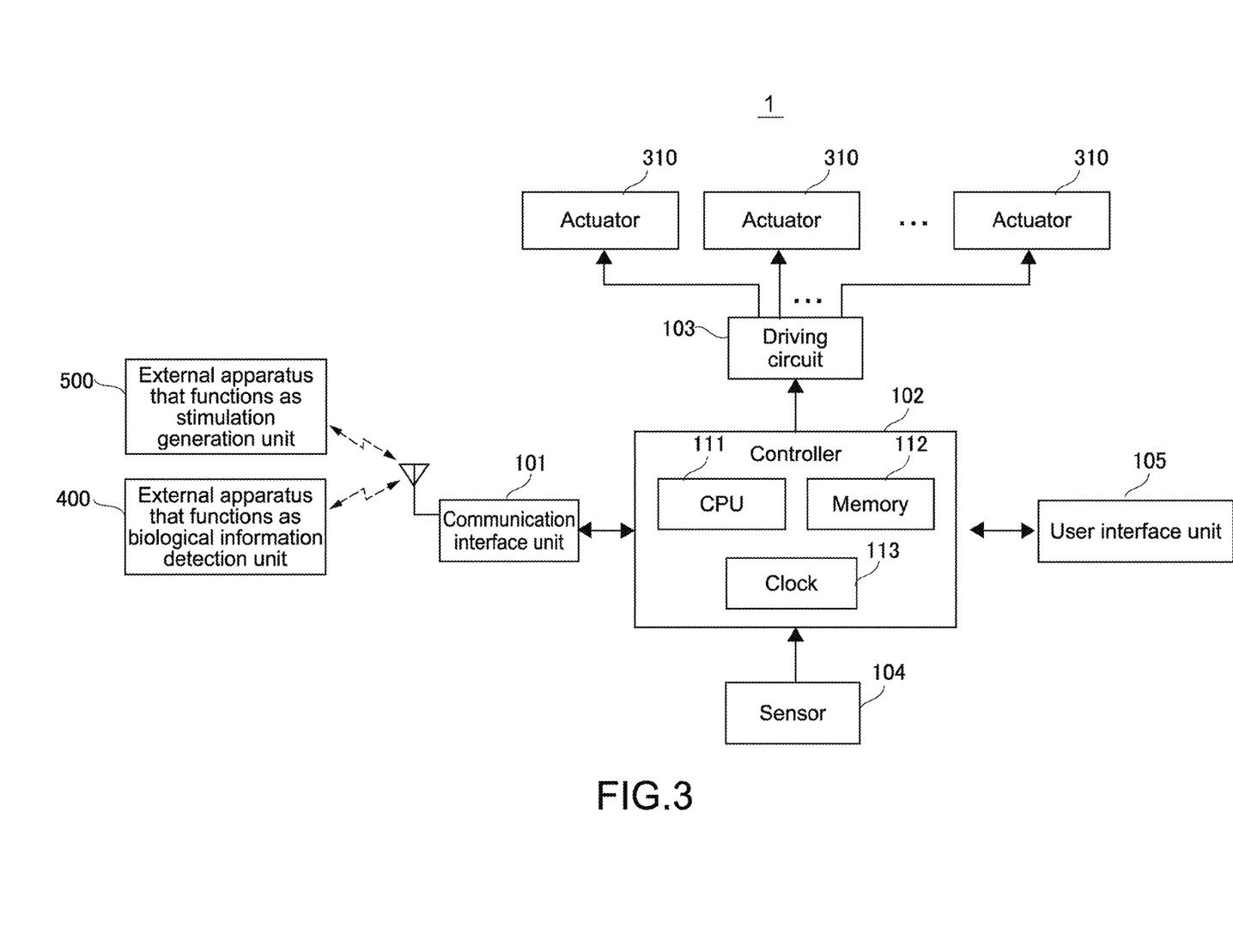
FIG. 3 A block diagram showing an electrical configuration of the sleep assistance apparatus 1 in FIG. 2.

FIG. 3 is a block diagram showing an electrical configuration of this sleep assistance apparatus 1 (sleep assistance system).

This sleep assistance apparatus 1 includes a plurality of actuators 310, 310, . . . , and 310, a communication interface unit 101, a controller 102, a driving circuit 103, one or more sensors 104, a user interface unit 105, a battery (not shown), and the like. Note that the sensors 104 correspond to the biological information detection unit 100. The controller 102 corresponds to the biological information evaluation unit 200. The actuators 310 correspond to the stimulation generation unit 300.

The communication interface unit 101, the controller 102, the driving circuit 103, the one or more sensors 104, and the battery (not shown) may be mounted on one actuator mounting unit 10, or separately placed on the plurality of actuator mounting units 10. The sensors 104 may be mounted on all of the actuator mounting units 10, or placed on the belts 11.

The actuator 310 is a mechanism that generates mechanical displacement for tactile stimulation. In this actuator 310, as tactile stimulation, for example, a "feeling of pressure" felt by the user U, which is obtained by causing a pressing part to move forward and backward toward the surface of a wrist of the user U to press the surface of the wrist of the user U, is used. The mechanical structure of the actuator that is capable of giving such tactile stimulation will be described later.

The driving circuit 103 generates driving current to be supplied to the actuators 310 on the basis of a control signal from the controller 102.

The communication interface unit 101 performs communication with an external apparatus 400 that functions as the biological information detection unit 100 and communication with an external home appliance equipment 500 that functions as the stimulation generation unit 300 through wired or wireless communication, for example. The external apparatus 400 that functions as the biological information detection unit 100 is, for example, an imaging apparatus and an image processing apparatus that analyzes an image picked up by the imaging apparatus, or a microphone that collects sound of snoring, bruxism, and the like of the user U.

The user interface unit 105 receives input of various kinds of data such as setting data from the user U and presents various kinds of information to the user U. The user interface unit 105 includes, for example, a display, a touch panel sensor (display 12 with a touch panel in FIG. 2) attached to the screen of the display, and the like.

The controller 102 includes a CPU 111, a memory 112, and a clock 113.

In the memory 112, in addition to the program that is executed by the CPU 111, the setting data given by the user U and the like are stored.

The clock 113 generates the present time data and supplies it to the CPU 111.

The CPU 111 performs the function as the biological information evaluation unit 200 in accordance with the program stored in the memory 112. Specifically, the CPU 111 decides the optimal stimulation depending on the stage of the sleep process on the basis of the biological information detected by the sensors 104 that corresponds to the biological information detection unit 100. The CPU 111 issues a control command to the stimulation generation unit 300 so that the decided stimulation is given to the user U.

[6. Structural Example of Actuator 310]

Next, a structural example of the actuator 310 that is capable of giving tactile stimulation caused by a feeling of pressure will be described.

Figure 4:
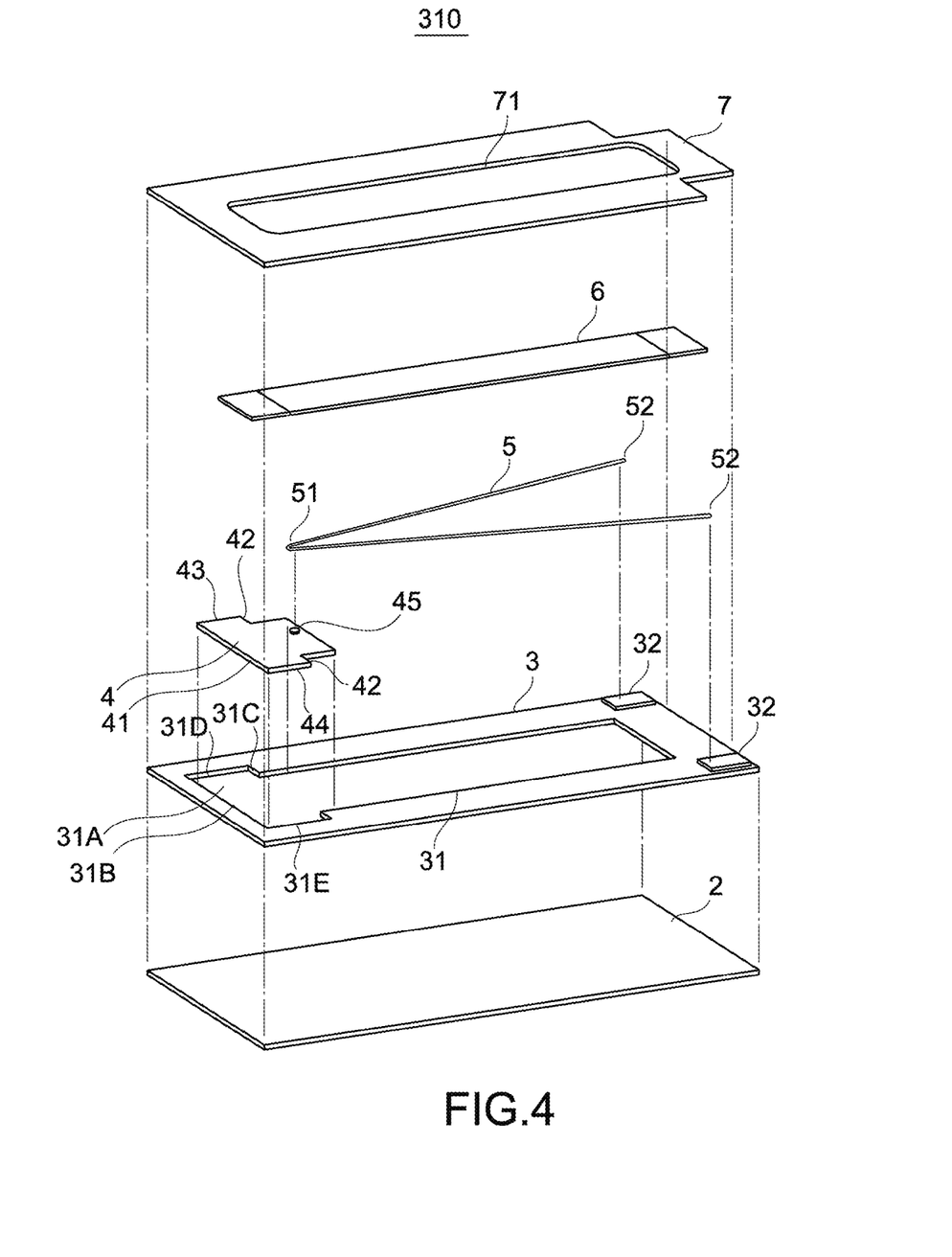
FIG. 4 An exploded perspective view showing the configuration of an actuator 310 as an example of a stimulation generation unit in FIG. 1

FIG. 4 is an exploded perspective view showing the configuration of the actuator 310.

Figure 5:
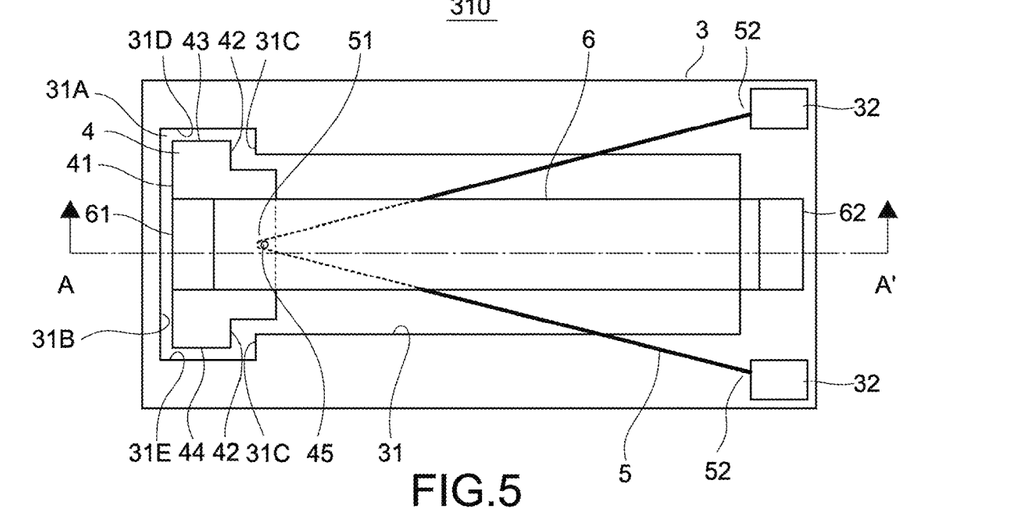
FIG. 5 A plan view showing the configuration of the actuator 310 in FIG. 4 excluding a base plate 2 and a top plate 7.

FIG. 5 is a plan view showing the configuration of the actuator 310 in FIG. 4 excluding a base plate 2 and a top plate 7.

Figure 6:
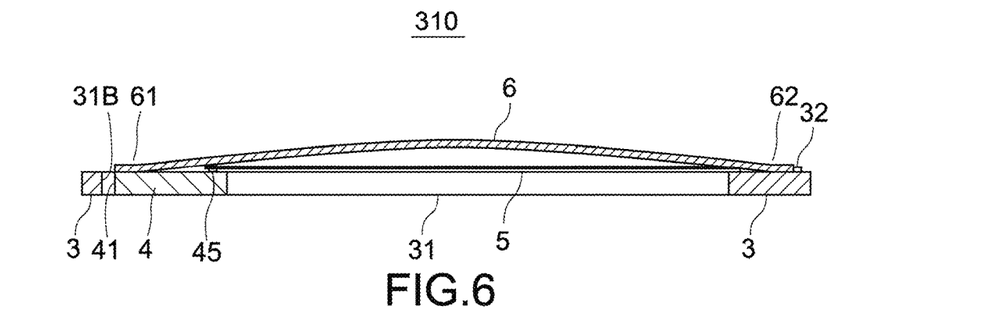
FIG. 6 A cross-sectional view of the actuator 310 in FIG. 4 and FIG. 5.

FIG. 6 is a cross-sectional view of the actuator 310 in FIG. 4 and FIG. 5.

As shown in these figures, this actuator 310 includes the base plate 2, a holder 3, a slider 4, a shape-memory alloy wire 5, an elastic plate 6, and the top plate 7.

The base plate 2 is formed of, for example, a rectangular thin plate member. On the base plate 2, the holder 3 is fixed.

The holder 3 is formed of, for example, a rectangular thin plate member. In the holder 3, an opening portion 31 is formed. One end portion of the opening portion 31 in an X-axis direction is used as a slider holding space 31A in which the slider 4 is slidably held in the X-axis direction. In more detail, the slider 4 has a thickness similar to that of the holder 3, and is three-dimensionally held in the three-dimensional space formed by the slider holding space 31A of the holder 3, the upper surface of the base plate 2, and the lower surface of the top plate 7.

The inner wall surface of the slider holding space 31A of the holder 3 functions as stopper surfaces 31B and 31C and slide guide surfaces 31D and 31E. The stopper surfaces 31B and 31C are respectively brought into contact with end surfaces 41 and 42 of the slider 4 in the X-axis direction to limit the sliding range. The slide guide surfaces 31D and 31E are respectively brought into contact with end surfaces 43 and 44 of the slider 4 in a Y-axis direction to guide the sliding.

The shape-memory alloy wire 5 is a wire formed of a shape-memory alloy. In this embodiment, one shape-memory alloy wire 5 bent in a V-shape at a central portion 51 is used. The central portion 51 of the shape-memory alloy wire 5 is locked at a locking portion 45 provided to the slider 4. End portions 52, 52 of the shape-memory alloy wire 5 are bonded to a pair of electrode units 32, 32 provided on the upper surface of the holder 3. Specifically, the shape-memory alloy wire 5 is placed to be pulled across a surface in parallel with the sliding surface of the slider 4. The pair of electrode units 32, 32 is provided on the surface of one end portion of the holder 3 in the X-axis direction. On the other end portion of the holder 3 in the X-axis direction, the slider holding space 31A is provided. In more detail, the pair of electrode units 32, 32 is provided at positions away from each other from the central position of the holder 3 in the Y-axis direction on the surface of the one end portion of the holder 3.

Figure 7:
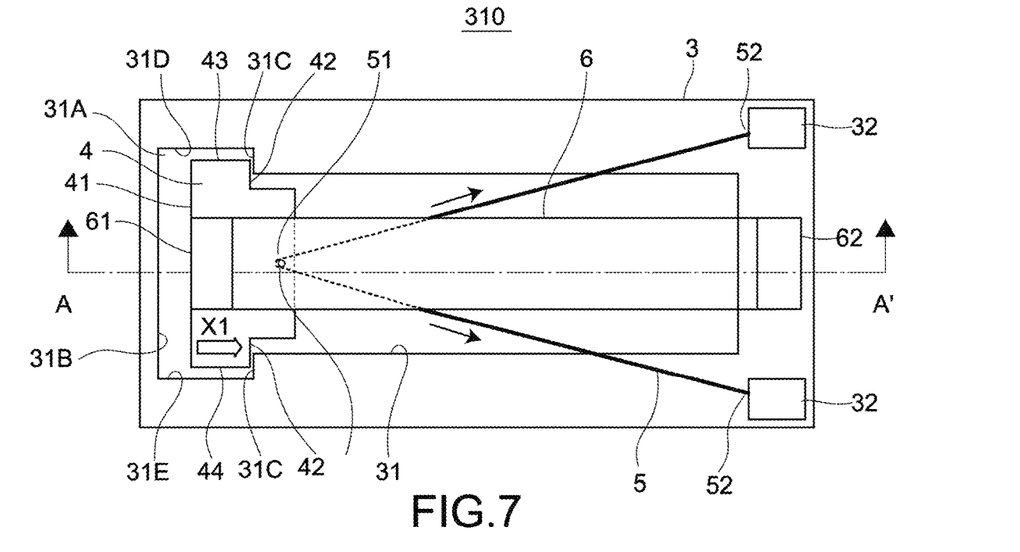
FIG. 7 A plan view showing the actuator 310 when being energized.
Figure 8:
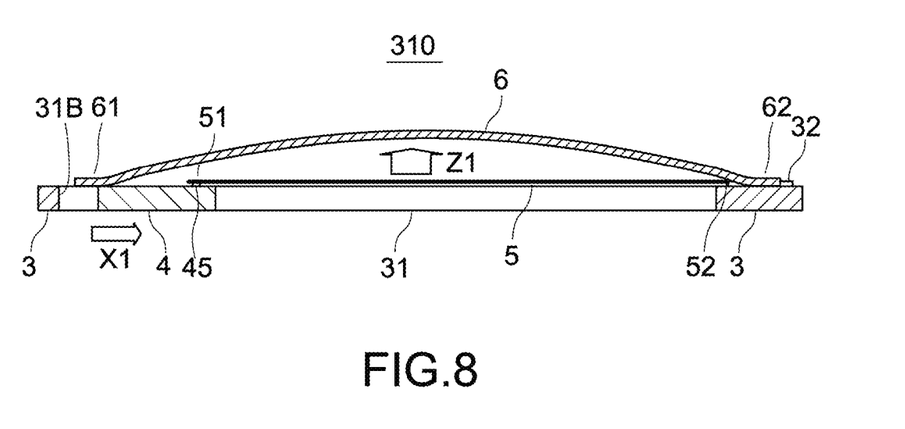
FIG. 8 A cross-sectional view showing the actuator 310 when being energized.

To the shape-memory alloy wire 5, current flows from a driving circuit (not shown) via the pair of electrode units 32, 32. When the temperature of the shape-memory alloy wire 5 has reached a predetermined temperature (specific temperature) by the joule heat generated by the current flowing through the shape-memory alloy wire 5, the shape-memory alloy wire 5 contracts in a line length direction. Since the central portion 51 of the shape-memory alloy wire 5 is locked at the locking portion 45 provided to the slider 4, the slider 4 is pulled toward the side of the bonding points of the end portions 52, 52 of the shape-memory alloy wire 5, and slides in an X1 direction in the slider holding space 31A when the shape-memory alloy wire 5 contracts in the line length direction, as shown in FIG. 7 and FIG. 8.

Further, when the energization to the shape-memory alloy wire 5 is stopped and the temperature of the shape-memory alloy wire 5 falls below the predetermined temperature (specific temperature), the shape-memory alloy wire 5 restores the original length before contraction. As a result, the slider 4 slides in the slider holding space 31A of the holder 3 in a direction opposite to the X1 direction and returns to the position shown in FIG. 5 and FIG. 6.

The elastic plate 6 (pressing portion) is formed of a thin plate elastic member. An end portion 61 of the elastic plate 6 is fixed to the slider 4, and the other end portion 62 of the elastic plate 6 is fixed to the one end portion of the holder 3 in the X-axis direction. On the other end portion of the holder 3 in the X-axis direction, the slider holding space 31A is provided.

The distance between the fixed points of the elastic plate 6 is changed along with sliding of the slider 4 in the X-axis direction. When the shape-memory alloy wire 5 is energized, the slider 4 slides in the slider holding space 31A in the X1 direction, and the distance between the fixed points of the elastic plate 6 is decreased. At this time, the elastic plate 6 is elastically deformed in a Z1 direction as shown in FIG. 5 by receiving pressure from the side of the fixed points, and thus is in a predetermined warped state.

In this actuator 310, slight warpage in the direction toward the top plate 7 (in the Z1 direction) is given to the elastic plate 6 as the initial distortion when the slider 4 is located at the position where the shape-memory alloy wire 5 is not energized (position shown in FIG. 5 and FIG. 6). Accordingly, it is possible to reliably make the elastic plate 6 in a predetermined warped state in which the elastic plate 6 is elastically deformed in the direction toward the top plate 7 (in the Z1 direction), when the shape-memory alloy wire 5 is energized.

When the slider 4 slides in the slider holding space 31A in the direction opposite to the X1 direction after the energization to the shape-memory alloy wire 5 is stopped, the distance between the fixed portions of the elastic plate 6 is increased. As a result, the elastic plate 6 returns to a slight warped state by the initial distortion.

The top plate 7 is formed of, for example, a rectangular thin plate member. At the position of the top plate 7, which substantially faces the elastic plate 6, an opening portion 71 is provided. This opening portion 71 is a portion for making at least a part of the elastic plate 6 in the predetermined warped state when the shape-memory alloy wire 5 is energized project to the position higher than the upper surface of the top plate 7.

As described above, in this actuator 310, it is possible to make the slider 4 slide by the movement of the contraction of the shape-memory alloy wire 5 in the line length direction when being energized, elastically deform the elastic plate 6 by decreasing the distance between the fixed points of the elastic plate 6 whose one end is fixed to this slider 4, and generate displacement in a direction perpendicular to the sliding surface of the slider 4 (in the Z-axis direction).

Figure 9:
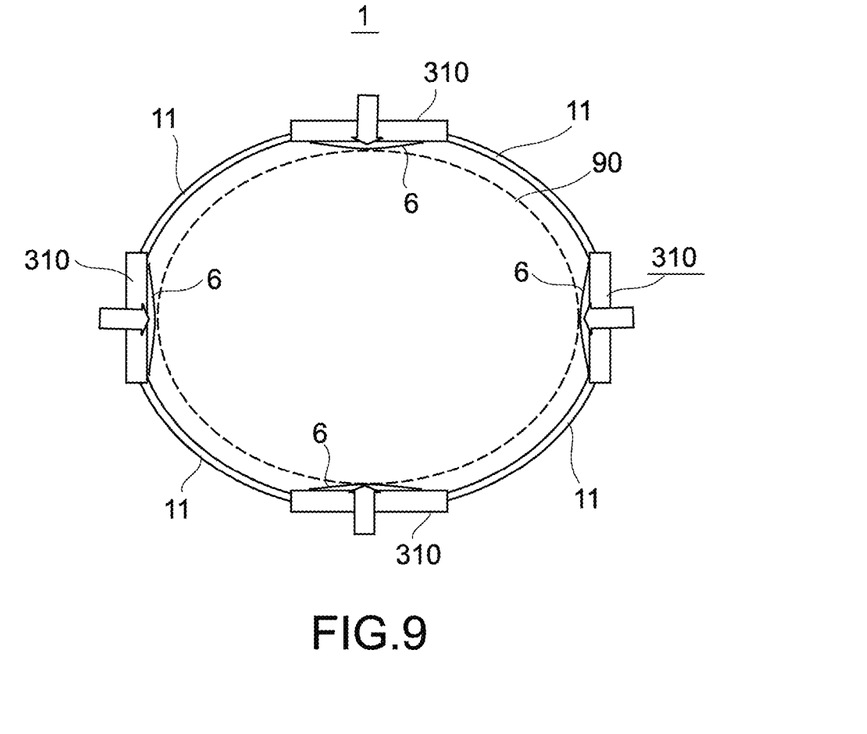
FIG. 9 An overall side view of the sleep assistance apparatus 1 configured by using the actuator 310.

FIG. 9 is an overall side view of the sleep assistance apparatus 1 configured by using the actuators 310.

The actuators 310 are coupled to each other by the belts 11 in series so that elastic plates 6 project toward the inside of the loop by being elastically deformed when it is attached to the wrist 90 of the user U.

The controller 102 outputs a control signal to the driving circuit 103 so that driving current is supplied to the actuators 310 at the same time. Accordingly, the elastic plates 6 of the actuators 310 are elastically deformed in synchronization with each other, and tactile stimulation caused by a feeling of pressure is concurrently given to the wrist of the user U.

[7. Example of Operation of Sleep Assistance Apparatus 1]

Next, the operation of the sleep assistance apparatus 1 according to this embodiment will be described.

In this operation example, assumption is made that the plurality of actuators 310 give tactile stimulation to the user U.

Figure 10:
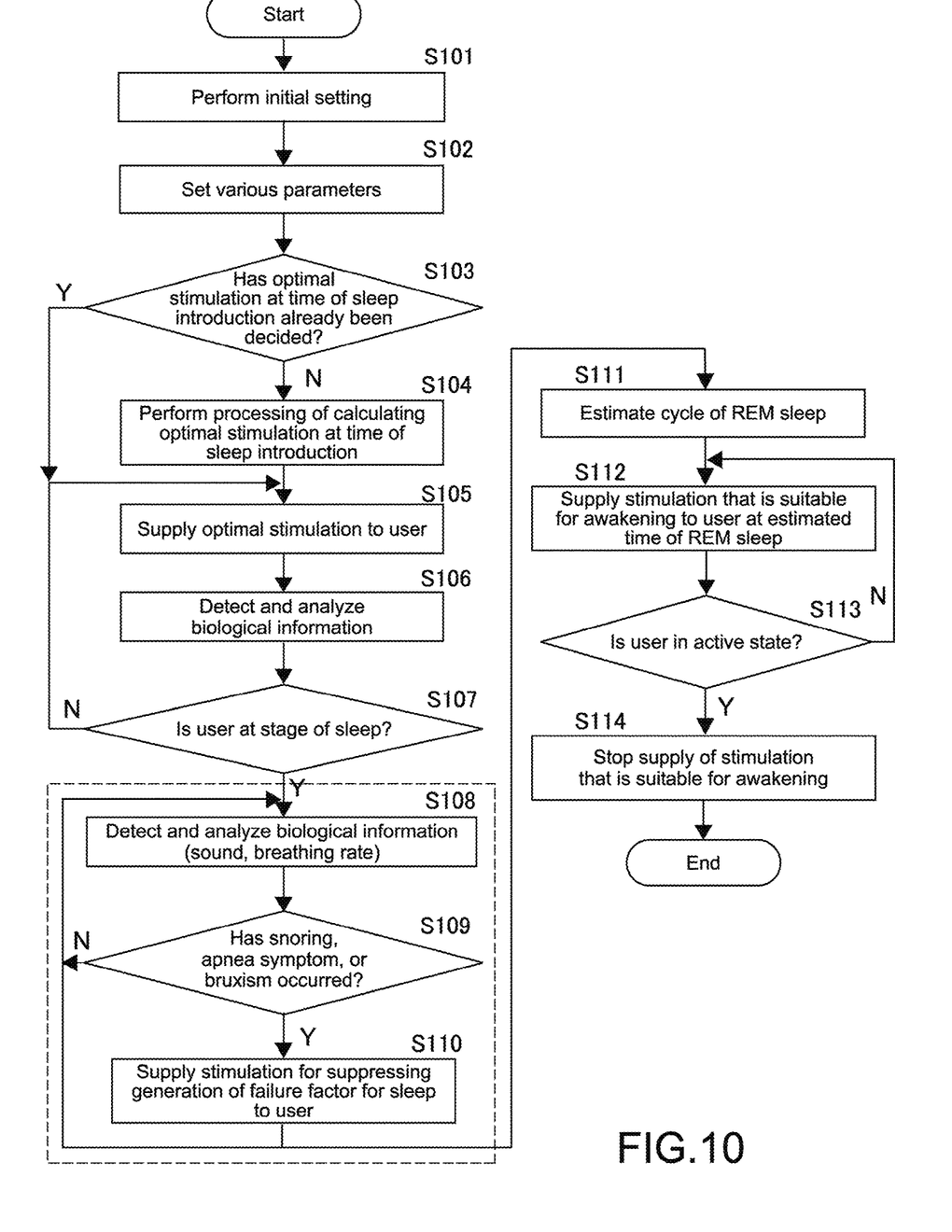
FIG. 10 A flowchart of the operation of the sleep assistance apparatus 1.

FIG. 10 is a flowchart of the operation of the sleep assistance apparatus 1.

At the time of the initial activation of the sleep assistance apparatus 1, the user U performs initial setting such as time adjustment of a clock 115 by using the user interface unit 105 (Step S101).

Next, the user U uses the user interface unit 105 to set parameters (Step 5102) such as:

a. get-up time;

b. candidate for stimulation at the time of the sleep introduction;

c. candidate for stimulation at the time of the awakening from sleep;

d. snooze setting (on/off, time interval, change in strength of stimulation, etc.) related to stimulation given at the time of the awakening from sleep; and e. snooze setting (on/off, time interval, etc.) of detection of activity of the user U.

When the user U performs an input operation for settling the setting content of the parameter by using the user interface unit 105, the controller 102 (CPU 111) stores the parameter information set by the user U in the memory 112. Then, the controller 102 performs service for the user U in the sleep process in accordance with the program stored in the memory 112.

Note that the set parameter information is stored in the memory 112 even when the main power supply of the sleep assistance apparatus 1 is turned off. Therefore, the user does not necessarily need to set the parameter information from the next time of the activation. In the case where the user U sets new parameter information, it is overwritten (updated) in the memory 112.

(7-1. Processing Related to Sleep Introduction)

As first service, processing of sleep introduction is started.

The controller 102 determines whether or not the optimal stimulation at the time of the sleep introduction has already been decided (Step S103). At the time of the initial activation of the sleep assistance apparatus 1, the optimal stimulation at the time of the sleep introduction is not decided (No in Step S103). Therefore, the controller 102 performs processing of deciding the optimal stimulation at the time of the sleep introduction from one or more candidates for stimulation for the sleep introduction set in advance (Step S104). The method of deciding the kind of the optimal sleep introduction stimulation will be described later in detail.

In the case where the optimal stimulation at the time of the sleep introduction has already been decided (Yes in Step S103), the controller 102 supplies a control command that includes information on the waveform pattern of the optimal stimulation at the time of the sleep introduction to the driving circuit 103. The driving circuit 103 generates driving current corresponding to this waveform pattern, and supplies it to the actuators 310. Accordingly, the actuators 310 give stimulation to the user U in accordance with the supplied waveform pattern (Step S105).

The controller 102 acquires the biological information detected by the sensor 104 while giving the optimal stimulation at the time of the sleep introduction to the user U, and analyzes it (Step S106). The controller 102 checks whether or not the user U is at the stage of sleep on the basis of the analysis result of the biological information (Step S107). At this time, the controller 102 may adjust the waveform pattern to be supplied to the driving circuit 103 so that tactile stimulation is given to the user U in synchronization with, for example, breathing or heartbeat on the basis of the acquired biological information.

(7-2. Processing of Deciding Optimal Stimulation at Time of Sleep Introduction)

Figure 11:
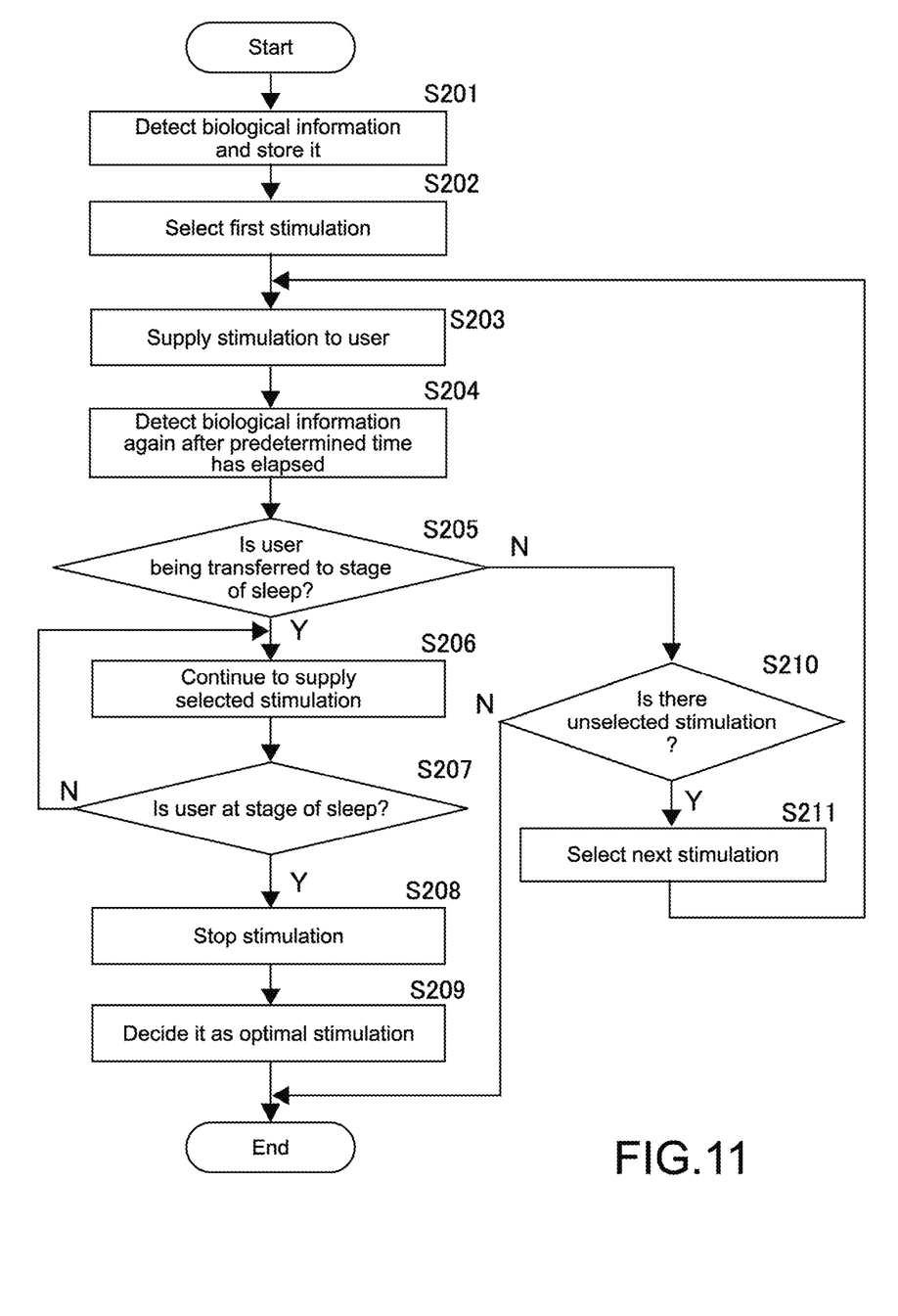
FIG. 11 A flowchart of processing of deciding optimal stimulation during sleep introduction.

FIG. 11 is a flowchart of processing of deciding the optimal stimulation at the time of the sleep introduction.

This processing is performed at the time of initial activation where the optimal stimulation at the time of the sleep introduction has not decided, in response to a command from the user U, or for each cycle of a predetermined period of time.

First, the controller 102 acquires the biological information at the time of awakening of the user U from the sensor 104 and stores it in the memory 112 (Step S201).

The controller 102 selects one stimulation from the one or more candidates for stimulation for the sleep introduction set in Step 5102 (Step S202), and supplies a control command including the information on the waveform pattern of the stimulation to the driving circuit 103, for example. The driving circuit 103 generates driving current corresponding to this waveform pattern, and supplies it to the actuators 310. Accordingly, the first stimulation is given to the user U (Step S203).

When a predetermined time has elapsed from the start of stimulation, the controller 102 acquires biological information from the sensors 104 again (Step S204), and determines whether or not the user U is being transferred to the stage of sleep on the basis of this biological information and the biological information detected before giving stimulation (Step S205).

When the controller 102 has determined that the user U is being transferred to the stage of sleep (Yes in Step S205), the controller 102 continues to supply the present selected stimulation until the user U is in the stage of sleep (Step S206).

When the user U is at the stage of sleep (Yes in Step S207), the controller 102 stops the supply of stimulation (Step S208), and decides the selected stimulation as the optimal stimulation at the time of the sleep introduction (Step S209).

On the other hand, when the controller 102 has determined that the user U is not being transferred to the stage of sleep even when a predetermined time has elapsed from the start of supply of stimulation in step 205 (No in Step S205), the controller 102 determines whether or not there is a candidate for unselected stimulation (Step S210). When there is unselected stimulation, the controller 102 selects one stimulation from the unselected stimulation (Step S211), and supplies it to the user U (Step S203). After that, similarly, the controller 102 acquires biological information from the sensor 104 again (Step 5204) after a predetermined time has elapsed, and repeats processing similar to that described above thereafter.

In the case where the effect of sleep introduction to the user U is not obtained even when all candidates of stimulation are tried (No in Step S210), processing of deciding the optimal stimulation is finished. In this case, on the user interface unit 105 (display 12 with a touch panel), failure of deciding the optimal stimulation is displayed. Accordingly, the user U is capable of trying any stimulation by setting other stimulation next time.

(7-3. Processing at Time of Sleep)

Now, return to the description of the flowchart shown in FIG. 10.

When determining that the user U is at the stage of sleep (Yes in Step S107), the controller 102 determines whether or not snoring, an apnea symptom, bruxism, or the like, which is a factor of blocking sound sleep, occurs, from the biological information detected by the sensor 104 such as a microphone and a respirometer (Step S).

When determining that snoring, an apnea symptom, bruxism, or the like has occurred (Yes in Step S109), the controller 102 performs control so as to give, to the user U, stimulation for suppressing the generation of the failure factor for sleep by causing the user U to change the posture (Step S110). This control is repeatedly performed during sleep. At this time, because there is also a case where the user gets used to certain stimulation and does not react with it, the strength of stimulation may be gradually increased or the kind of stimulation may be changed.

(7-4. Processing During Get-Up)

The controller 102 estimates the cycle of REM sleep of the user U since a predetermined time before the get-up time set by the user U on the basis of the biological information detected by the sensors 104 (Step S111).

The controller 102 estimates the REM sleep time closest to set get-up time before the set get-up time on the basis of the estimation result of the REM cycle and get-up time set by the user U in advance. Then, the controller 102 performs control so as to give stimulation that is suitable for awakening (awakening from sleep) at the estimated time of REM sleep (Step S112).

After that, the controller 102 determines whether or not the user U is in an active state (actually gets up) after the user U has awaked (Step S113). This determination is performed in such a way that, for example, the controller 102 receives a notification of being in an active state from the user U via the user interface unit 105. Alternatively, the determination may be performed on the basis of the biological information detected by the sensors 104.

Incidentally, in this sleep assistance apparatus 1, a snooze function related to stimulation provision for the awakening from sleep is provided. For the snooze function, the user U is capable of setting on/off, a time interval, a change in strength of stimulation, and the like, in advance.

In the case where the snooze function is set to be on, the controller 102 determines whether or not the user U is in an active state at the point when the set time has elapsed from when tactile stimulation that is suitable for the previously performed awakening (awakening from sleep) has occurred. Note that this set time is decided within a range shorter than the time interval set for the snooze function related to stimulation provision for the awakening from sleep.

In the case where it is determined that the state of the user U has been transferred to an active state (Yes in Step S113), the controller 102 performs control so as to stop the supply of stimulation for awakening (Step S114).

In the case where it is determined that the state of the user has not transferred to an active state (No in Step S113), the controller 102 performs control so as to give tactile stimulation that is suitable for awakening (awakening from sleep) again. This control is similarly repeated when the state of the user U has not transferred to an active state similarly even at the time when the set time has elapsed next time. Further, in the case where a change in the strength of stimulation is set by the user U, the controller 102 performs control so as to gradually increase the strength of stimulation every time the number of giving tactile stimulation is increased. The method of changing the strength of stimulation includes a method of changing amplitude, acceleration, rhythm, and the like.

Further, as another method of determining whether or not the state of the user U has transferred to an active state, there is a method of causing the user U to input a password. Alternatively, transferring to an active state may be determined by the combination of determination of transferring to an active state based on the biological information detected the sensor 104 and inputting of a password.

Because the sleep assistance apparatus 1 according to this embodiment is configured as described above, the following effects are promising.

1. The sleep assistance apparatus 1 automatically searches for stimulation that is suitable for the user U at the time of the sleep introduction, and employs it. Accordingly, it is expected to be able to quickly introduce the user U into a sleep state.

2. The sleep assistance apparatus 1 is capable of detecting that a symptom such as snoring, bruxism, and an apnea symptom has occurred during sleep, and giving tactile stimulation for causing the user U to unconsciously change the posture. Accordingly, it is possible to prevent snoring, bruxism, and an apnea symptom from occurring.

3. The sleep assistance apparatus 1 estimates REM sleep time closest to set get-up time before the get-up time set by the user U in advance, and gives tactile stimulation that is suitable for awakening at this time. Accordingly, it is expected to be able to provide comfortable awakening to the user U.

It should be noted that the present technology may take the following configurations.

(1) A sleep assistance apparatus, including: a stimulation generation unit that generates stimulation, a user being capable of receiving the stimulation;

a detection unit that detects biological information of the user; and a control unit that decides optimal stimulation on the basis of the detected biological information, and causes the stimulation generation unit to generate the optimal stimulation.

(2) The sleep assistance apparatus according to (1) above, in which the control unit is configured to cause the stimulation generation unit to generate a plurality of kinds of stimulation in order, evaluate the detected biological information every time the stimulation is generated, and determine the optimal stimulation for sleep introduction.

(3) The sleep assistance apparatus according to (2) above, in which the control unit is configured to determine presence or absence of generation of a failure factor for sleep on the basis of the detected biological information during the sleep, and cause the stimulation generation unit to generate specific stimulation when the generation of the failure factor is detected.

(4) The sleep assistance apparatus according to (3) above, in which the detection unit is configured to detect sound derived from the user during the sleep as the biological information, and the control unit is configured to determine presence or absence of the generation of the failure factor for sleep on the basis of the detected sound.

(5) The sleep assistance apparatus according to (3) above, in which the detection unit is configured to detect a breathing rate of the user during the sleep as the biological information, and the control unit is configured to determine presence or absence of the generation of the failure factor for sleep on the basis of the detected breathing rate.

(6) The sleep assistance apparatus according to any one of (1) to (5) above, in which the stimulation generation unit, the stimulation generation unit, and the control unit are integrally formed as a unit that is freely attached and detached to/from the user.

REFERENCE SIGNS LIST 1 sleep assistance apparatus
100 biological information detection unit
101 communication interface unit
102 controller
103 driving circuit
104 sensor
105 user interface unit
200 biological information evaluation unit
300 stimulation generation unit
310 actuator
500 home appliance equipment

The invention claimed is:

1. A sleep assistance apparatus, comprising:
at least one actuator configured to generate a plurality of kinds of stimulation;
at least one sensor configured to detect user biological information; and
a central processing unit (CPU) configured to:
determine a sleep stage of a user sleep process is a deep sleep stage;
select a first kind of stimulation, from the plurality of kinds of stimulation, based on the detected user biological information and the determined deep sleep stage of the user sleep process;
control the at least one actuator to generate the first kind of stimulation;
estimate a user cycle of rapid eye moment (REM) sleep based on the user biological information;
determine REM sleep time based on the estimated user cycle of REM sleep; and
control the at least one actuator to generate a second kind of stimulation based on the determined REM sleep time.

2. The sleep assistance apparatus according to claim 1, wherein the CPU is further configured to:
determine one of presence or absence of generation of a failure factor for sleep based on the detected user biological information; and
control the at least one actuator to generate the second kind of stimulation based on the determination that the generation of the failure factor is present.

3. The sleep assistance apparatus according to claim 2, wherein
the at least one sensor is further configured to detect user sound derived in the sleep stage as the user biological information, and
the CPU is further configured to determine one of presence or absence of the generation of the failure factor for sleep based on the detected user sound.

4. The sleep assistance apparatus according to claim 2, wherein
the at least one sensor is further configured to detect a user breathing rate in the sleep stage as the user biological information, and
the CPU is further configured to determine one of presence or absence of the generation of the failure factor for sleep based on the detected user breathing rate.

5. The sleep assistance apparatus according to claim 1, wherein
the at least one actuator, the at least one sensor, and the CPU are integrated as a freely attachable and detachable user unit.

6. The sleep assistance apparatus according to claim 1, wherein the user biological information includes one of user sound, a user breathing rate, user body temperature, a user motion, or an image of user eyeballs.

7. The sleep assistance apparatus according to claim 1, wherein the at least one actuator is further configured to generate the plurality of kinds of stimulation based on a mechanical displacement of the at least one actuator.

8. A sleep assistance method, comprising:
generating, by at least one actuator, a plurality of kinds of stimulation;
detecting, by at least one sensor, user biological information;
determining, by a central processing unit (CPU), a sleep stage of a user sleep process is a deep sleep stage;
selecting, by the CPU, a specific kind of stimulation, from the plurality of kinds of stimulation, based on the detected user biological information and the determined deep sleep stage of the user sleep process;
controlling, by the CPU, the at least one actuator to generate the specific kind of stimulation;
estimating, by the CPU, a user cycle of rapid eye moment (REM) sleep based on the user biological information;
determining, by the CPU, REM sleep time based on the estimated user cycle of REM sleep; and controlling, by the CPU, the at least one actuator to generate a second kind of stimulation based on the determined REM sleep time.

\* \* \* \* \*